United States Patent
Taeschler et al.

(10) Patent No.: US 11,530,175 B2
(45) Date of Patent: Dec. 20, 2022

(54) METHOD FOR PREPARATION OF FLUORO ALKYLATED COMPOUNDS BY HOMOGENEOUS NI CATALYSIS

(71) Applicant: Lonza Solutions AG, Visp (CH)

(72) Inventors: Christoph Taeschler, Visp (CH); Stefan Ellinger, Visp (CH); Florencio Zaragoza Doerwald, Buochs (CH); Matthias Beller, Nienhagen (DE); Helfried Neumann, Rostock (DE); Florian Fischer, Rostock (DE); Shaoke Zhang, Rostock (DE); Nicolas Rotta-Loria, Vancouver (CA)

(73) Assignee: ARXADA AG, Visp (CH)

( * ) Notice: Subject to any disclaimer, the term of this patent is extended or adjusted under 35 U.S.C. 154(b) by 0 days.

(21) Appl. No.: 17/424,193

(22) PCT Filed: Feb. 20, 2020

(86) PCT No.: PCT/EP2020/054542
§ 371 (c)(1),
(2) Date: Jul. 20, 2021

(87) PCT Pub. No.: WO2020/169768
PCT Pub. Date: Aug. 27, 2020

(65) Prior Publication Data
US 2022/0041530 A1 Feb. 10, 2022

Related U.S. Application Data

(60) Provisional application No. 62/807,899, filed on Feb. 20, 2019.

(30) Foreign Application Priority Data

Feb. 20, 2019 (EP) .................................... 19158332

(51) Int. Cl.
| | |
|---|---|
| *C07C 17/32* | (2006.01) |
| *B01J 31/22* | (2006.01) |
| *B01J 31/24* | (2006.01) |
| *C07C 41/30* | (2006.01) |
| *C07C 209/74* | (2006.01) |
| *C07C 213/08* | (2006.01) |
| *C07D 207/33* | (2006.01) |
| *C07D 213/60* | (2006.01) |
| *C07D 213/69* | (2006.01) |
| *C07D 233/64* | (2006.01) |
| *C07D 333/12* | (2006.01) |

(52) U.S. Cl.
CPC ........... *C07C 17/32* (2013.01); *B01J 31/2295* (2013.01); *B01J 31/2409* (2013.01); *C07C 41/30* (2013.01); *C07C 209/74* (2013.01); *C07C 213/08* (2013.01); *C07D 207/33* (2013.01); *C07D 213/60* (2013.01); *C07D 213/69* (2013.01); *C07D 233/64* (2013.01); *C07D 333/12* (2013.01); *B01J 2531/847* (2013.01)

(58) Field of Classification Search
CPC ....................................................... C07C 17/32
USPC ......................................................... 546/296
See application file for complete search history.

(56) References Cited

U.S. PATENT DOCUMENTS 10,968,187 B2 * 4/2021 Taeschler ............. C07D 207/33

OTHER PUBLICATIONS

Butcher, Angew. Chem. Int. Ed.2021, 60, 2-27.*
Zhang, Chem. Commun., 2020, 56, 15157-15160.*
International Search Report and Written Opinion for PCT/EP2020/054542 dated Apr. 9, 2020, 12 pages.
Loy et al, "Palladium-Catalyzed C—H Perfluoroalkylation of Arenes," Organic Letters, vol. 13, May 1, 2024, pp. 2548-2551.
Standley et al., "A Broadly Applicable Strategy for Entry into Homogeneous Nickel(0) Catalysts from Air-Stable Nickel(II) Complexes," Organometallics, Apr. 16, 2014, pp. 2012-2018.

* cited by examiner

*Primary Examiner* — Nizal S Chandrakumar
(74) *Attorney, Agent, or Firm* — Dority & Manning, P.A.

(57) ABSTRACT

The invention discloses a method for the preparation of fluoro alkylated compounds by homogeneous Ni catalyzed fluoro alkylation with fluoro alkyl halides in the presence of a base.

11 Claims, No Drawings

METHOD FOR PREPARATION OF FLUORO ALKYLATED COMPOUNDS BY HOMOGENEOUS NI CATALYSIS

CROSS REFERENCE TO RELATED APPLICATIONS

This application is the U.S. National Stage entry of International Application Number PCT/EP2020/054542 filed under the Patent Cooperation Treaty having a filing date of Feb. 20, 2020, which claims priority to U.S. Provisional Patent Application No. 62/807,899 having a filing date of Feb. 20, 2019, and European Patent Application No. 19158332.7 having a filing date of Feb. 20, 2019, which are incorporated herein by reference.

TECHNICAL FIELD

The invention discloses a method for the preparation of fluoro alkylated compounds by homogeneous Ni catalyzed fluoro alkylation with fluoro alkyl halides in the presence of a base.

BACKGROUND OF THE INVENTION

Organofluorine chemistry plays an important role in medicinal, agricultural, and material sciences and fields. Fluoroalkyl groups have strong effects such as high stability and lipophilicity, in addition, longer fluoroalkyl groups have high water and oil resistance and low friction.

Loy, R. N., et al., Organic Letters 2011, 13, 2548-2551, discloses Pd-catalyzed coupling of $CF_3$—I with benzene in 26% GC yield.

According to Table 1 entry 10 the coupling of $C_6F_{13}I$ provided 81% yield.

But a repetition of this experiment with the bromide instead of the iodide provided less than 1% yield, see Comparative Example herein.

There was a need for a homogenous catalyzed method for the preparation of fluoro alkylated compounds by direct C—H fluoro methylation, which provides high yields but does not need the assistance of a directing group or of electron rich aromatic compounds. The method should be applicable to a wide variety of substrates and should be compatible with a wide variety of functional groups. Furthermore the method should not be restricted to iodides as alkylating agents only, but should also work with bromides.

Unexpectedly a reaction with homogenous Ni catalysis was found that meets these requirements. No dialkylated products are observed. Only small exchange of the halide against H in the fluoro alkylated halide is observed.

ABBREVIATIONS

In this text, the following meanings are used, if not otherwise stated:
alkyl linear or branched alkyl, preferably linear;
DME 1,2-dimethoxyethane
dppb 1,4-Bis(diphenylphosphino)butane, compound 0 formula (dppb)

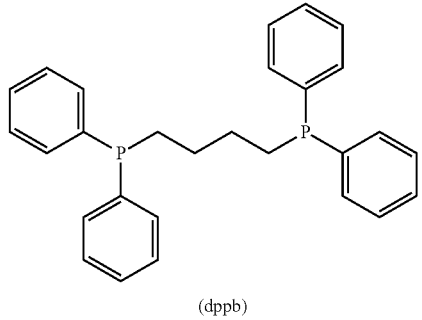 [SMILES: c1ccc(P(CCCCP(c2ccccc2)c2ccccc2)c2ccccc2)cc1]

(dppb)

dppf 1,1'-Bis(diphenylphosphino)ferrocen, compound of formula (4)

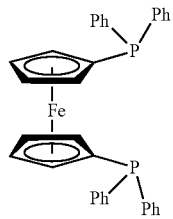

(4)

eq, equiv equivalent
halogen F, Cl, Br or I; preferably F, Cl or Br; more preferably F or Cl
"linear" and "n-" are used synonymously with respect to the respective isomers of alkanes
MTBE methyl tert-butyl ether
Ni-cat2 (dppf)Ni(o-tol)Cl
PfP-H 1,1,1,2,3,3,3-heptafluoropropane
PhB-acid Phenylboronic acid, compound of formula (5)

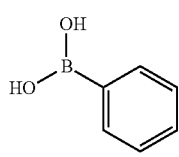

(5)

PhbP triphenylphosphine
PMHS polymethylhydrosiloxane
RT room temperature, it is used synonymously with the expression ambient temperature
"wt %", "% by weight" and "weight-%" are used synonymously and mean percent by weight

SUMMARY OF THE INVENTION

Subject of the invention is a method for the preparation of a fluoro alkylated compound FACOMPSUBST by a reaction of a compound COMPSUBST with a fluoro alkyl halide FAHALIDE by homogeneous catalysis using a Ni catalyst NICAT in the presence of a base BAS;
wherein
NICAT is Ni-cat1 or Ni-cat2;
Ni-cat1 is a combination of a nickel salt NISALT with a ligand LIG
NISALT is $NiCl_2$ or $Ni(NO_3)_2$;

LIG is selected from the group consisting of compound of formula (DPEPhos), compound of formula (dppb) and Ph₃P;

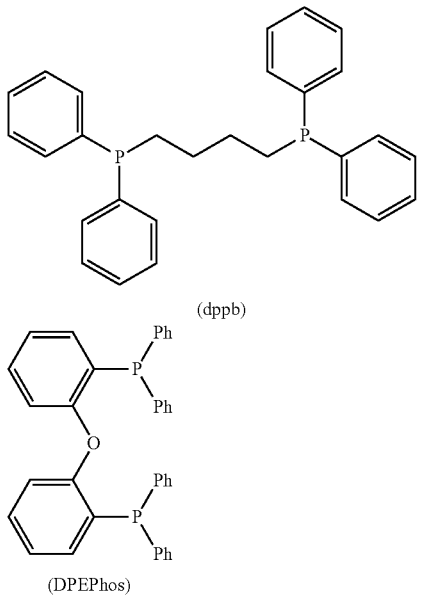

Ni-cat2 is compound of formula (Ni-cat2);

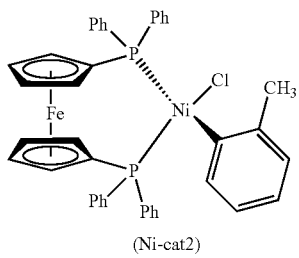

BAS is selected from the group consisting of $Cs_2CO_3$, $CsHCO_3$, $K_3PO_4$, NaH and NaOtBu;

FAHALIDE is a compound of formula (FAHALIDE);

$$X2\text{-}R3\text{-}X1 \qquad \text{(FAHALIDE)}$$

R3 is $C_{1-20}$ alkylen, wherein in the alkylen chain at least one of the hydrogens is substituted by F;

X1 is Br or I;

X2 is Br or H;

COMPSUBST is selected from the group consisting of a compound COMPSUBST-I, ethene, cyclohexene, ethine, and polystyrene;

the ethene and the cyclohexene being unsubstituted or substituted by 1, 2 or 3 substituents selected from the group consisting of $C_{1-10}$ alkyl, $C_{3-8}$ cycloalkyl, $C_{1-4}$ alkoxy, N(R10)R11, CN, NO, $NO_2$, F, Cl, Br, I, $CF_3$, $(CH_2)_m$—C(O)Y1, $S(O)_2$R50, CH=C(H)R28, C≡C—R24, benzyl, phenyl, naphthyl and morpholine;

the ethine being unsubstituted or substituted by 1 substitutent selected from the group consisting of $C_{1-10}$ alkyl, $C_{3-8}$ cycloalkyl, $C_{1-4}$ alkoxy, N(R10)R11, CN, NO, $NO_2$, F, Cl, Br, I, $CF_3$, $(CH_2)_m$—C(O)Y1, $S(O)_2$R50, CH=C(H)R28, C≡C—R24, benzyl, phenyl and naphthyl;

COMPSUBST-I is a compound of formula (COMPSUBST-I)

$$\text{RINGA} \qquad \text{(COMPSUBST-I)}$$

RINGA is an aromatic 5 or 6 membered carbocyclic or heterocyclic ring, when RINGA is a heterocyclic ring, then RINGA has 1, 2 or 3 identical or different endocyclic heteroatoms independently from each other selected from the group consisting of N, O and S, when RINGA is a 5 membered ring, then RINGA is unsubstituted or substituted by 1, 2, 3 or 4 identical or different substitutents, when RINGA is a 6 membered ring then RINGA is unsubstituted or substituted by 1, 2, 3, 4 or 5 identical or different substitutents, any of said substitutents of RINGA is independently from any other of said substitutents of RINGA selected from the group consisting of $C_{1-10}$ alkyl, $C_3$-8 cycloalkyl, $C_{1-4}$ alkoxy, OH, N(R10)R11, CN, NH—OH, NO, $NO_2$, F, Cl, Br, I, $CF_3$, $(CH_2)_m$—C(O)Y1, $S(O)_2$R50, CH=C(H)R28, C≡C—R24, benzyl, phenyl and naphthyl;

RINGA can be condensed with a ring RINGB, RINGB is a 5 or 6 membered carbocyclic or heterocyclic ring, when RINGB is a heterocyclic ring, is contains 1, 2 or 3 identical or different endocyclic heteroatoms independently from each other selected from the group consisting of N, O and S;

when RINGB is a 5 membered ring, then RINGB is unsubstituted or substituted by 1, 2 or 3 identical or different substitutents, when RINGB is a 6 membered ring then RINGB is unsubstituted or substituted by 1, 2, 3 or 4 identical or different substitutents, any of said substitutents of RINGB is independently from any other of said substitutents of RINGB selected from the group consisting of $C_{1-10}$ alkyl, $C_{3-8}$ cycloalkyl, $C_{1-4}$ alkoxy, OH, N(R17)R18, CN, NH—OH, NO, $NO_2$, F, Cl, Br, I, $CF_3$, $(CH_2)_n$—C(O)Y2, $S(O)_2$R51, CH=C(H)R38, C≡C—R34, benzyl, phenyl and naphthyl;

any of said $C_{1-10}$ alkyl substitutent of RINGA or RINGB is unsubstituted or substituted with 1, 2, 3, 4 or 5 identical or different substituents selected from the group consisting of halogen, OH, O—C(O)—$C_{1-5}$ alkyl, O—$C_{1-10}$ alkyl, S—$C_{1-10}$ alkyl, S(O)—$C_{1-10}$ alkyl, $S(O_2)$—$C_{1-10}$ alkyl, O—$C_{1-6}$ alkylen-O—$C_{1-6}$ alkyl, $C_{3-8}$ cycloalkyl and 1,2,4-triazolyl;

any of said benzyl, phenyl and naphthyl substitutent of RINGA or RINGB is independently from each other unsubstituted or substituted with 1, 2, 3, 4 or 5 identical or different substituents selected from the group consisting of halogen, $C_{1-4}$ alkoxy, $NO_2$ and CN;

m and n are identical or different and independently from each other 0, 1, 2, 3, 4, 5, 6, 7, 8, 9 or 10;

Y1 and Y2 are identical or different and independently from each other selected from the group consisting of H, OH, C(R14)(R15)R16, $C_{1-6}$ alkyl, O—$C_{1-6}$ alkyl, phenyl, benzyl, O-phenyl, O—$C_{1-6}$ alkylen-O—$C_{1-6}$ alkyl and N(R19)R20;

R14, R15 and R16 are identical or different and independently from each other selected from the group consisting of H, F, Cl and Br;

R10, R11, R17, R18, R19 and R20 are identical or different and are independently from each other H or $C_{1-6}$ alkyl, or R10 and R11, R17 and R18 or R19 and R20 represent together a tetramethylene or a pentamethylene chain;

R50 and R51 are identical or different and independently from each other selected from the group consisting of OH, $C_{1-6}$ alkyl and $C_{1-6}$ alkoxy;

R24, R34, R28 and R38 are identical or different and independently from each other selected from the group consisting of H, $C_{1-10}$ alkyl, C(R25)(R26)-O—R27;

R25, R26 and R27 are identical or different and independently from each other selected from the group consisting of H and $C_{1-10}$ alkyl.

DETAILED DESCRIPTION OF THE INVENTION

Preferably, when LIG is $Ph_3P$ then NISALT is $Ni(NO_3)_2$.

Preferably, when LIG is compound of formula (dppb) then NISALT is $NiCl_2$.

Preferably, LIG is compound of formula (DPEPhos) or $Ph_3P$.

Preferably, $Ni(NO_3)_2$ is used in form of its hydrate $Ni(NO_3)_2\ 6H_2O$.

$NiCl_2$ can be used as such or as $NiCl_2(DME)$; $NiCl_2(DME)$ is a mixture of $NiCl_2$ and 1,2-dimethoxyethane in the molar ratio of 1:1;

preferably $NiCl_2$ is used as $NiCl_2(DME)$.

Preferably, BAS is selected from the group consisting of $Cs_2CO_3$, $K_3PO_4$, NaH and NaOtBu; more preferably, BAS is $Cs_2CO_3$ or $K_3PO_4$, when COMPSUBST is COMPSUBST-I or polystyrene;

BAS is NaH or NaOtBu, when COMPSUBST is the ethene, the cyclohexene or the ethine.

Preferably, m and n are identical or different and independently from each other 0, 1, 2, 3 or 4; more preferably, m and n are identical or different and independently from each other 0 or 4.

Preferably, Y1 and Y2 are identical or different and independently from each other selected from the group consisting of H, OH, $C_{1-2}$ alkyl, and O—$C_{1-2}$ alkyl.

Preferably, COMPSUBST is selected from the group consisting of compound COMPSUBST-I, ethene, cyclohexene, ethine, and polystyrene;

the ethene and the cyclohexene being unsubstituted or substituted by 1 or 2 substitutents selected from the group consisting of $C_{1-10}$ alkyl, $C_{3-6}$ cycloalkyl, $C_{1-4}$ alkoxy, N(R10)R11, CN, F, Cl, Br, I, $CF_3$, $(CH_2)_m$—C(O)Y1, $S(O)_2R50$, benzyl, phenyl, naphthyl and morpholine;

the ethine being unsubstituted or substituted by 1 substitutent selected from the group consisting of $C_{1-10}$ alkyl, $C_{3-6}$ cycloalkyl, $C_{1-4}$ alkoxy, N(R10)R11, CN, F, Cl, Br, I, $CF_3$, $(CH_2)_m$—C(O)Y1, $S(O)_2R50$, benzyl, phenyl and naphthyl;

with COMPSUBST-I being selected from the group consisting of with COMPSUBST-I being unsubstituted or substituted by 1, 2, 3 or 4 in case of COMPSUBST-I being a monocyclic compound with 5 endocyclic atoms, by 1, 2, 3, 4 or 5 in case of COMPSUBST-I being a monocyclic compound with 6 endocyclic atoms, by 1, 2, 3, 4, 5 or 6 in case of COMPSUBST-I being a bicyclic compound wherein a 5-membered and a 6-membered ring are ortho-fused, by 1, 2, 3, 4, 5, 6 or 7 in case of COMPSUBST-I being a bicyclic compound wherein two 6-membered rings are ortho-fused, identical or different substituents independently from each other selected from the group consisting of $C_{1-10}$ alkyl, $C_{3-8}$ cycloalkyl, $C_{1-4}$ alkoxy, OH, C(H)=O, N(R10)R11, CN, NH—OH, NO, $NO_2$, F, Cl, Br, I, $CF_3$, $(CH_2)_m$—C(O)Y1, $S(O)_2R50$, CH=C(H)R28, C≡C—R24, benzyl, phenyl and naphthyl;

said $C_{1-10}$ alkyl substitutent of COMPSUBST-I is unsubstituted or substituted with 1, 2, 3, 4 or 5 identical or different substituents selected from the group consisting of halogen, OH, O—C(O)—$C_{1-5}$ alkyl, O—$C_{1-10}$ alkyl, S—$C_{1-10}$ alkyl, S(O)—$C_{1-10}$ alkyl, $S(O_2)$—$C_{1-10}$ alkyl, O—$C_{1-6}$ alkylen-O—$C_{1-6}$ alkyl, $C_{3-8}$ cycloalkyl and 1,2,4-triazolyl;

said benzyl, phenyl and naphthyl substitutents of COMPSUBST-I are independently from each other unsubstituted or substituted with 1, 2, 3, 4 or 5 identical or different substituents selected from the group consisting of halogen, $C_{1-4}$ alkoxy, $NO_2$ and CN;

with R10, R11, m, Y1, R28, R50, R24 and halogen as defined herein, also with all their embodiments.

More preferably, COMPSUBST-I is unsubstituted or substituted by 1, 2 or 3 in case of COMPSUBST-I being a monocyclic compound with 5 endocyclic atoms, by 1, 2, 3, 4 or 5 in case of COMPSUBST-I being a monocyclic compound with 6 endocyclic atoms, by 1, 2, 3 or 4 in case of COMPSUBST-I being a bicyclic compound wherein a 5-membered and a 6-membered ring are ortho-fused, by 1, 2, 3, 4 or 5 in case of COMPSUBST-I being a bicyclic compound wherein two 6-membered rings are ortho-fused, identical or different substituents independently from each other selected from the group consisting of $C_{1-4}$ alkyl, $C_{1-4}$ alkoxy, OH, C(H)=O, N(R10)R11, CN, F, Cl, Br, $CF_3$, $(CH_2)_m$—C(O)Y1, and $S(O)_2R50$;

said $C_{1-4}$ alkyl substitutent of COMPSUBST-I is unsubstituted or substituted with 1, 2 or 3 identical or different substituents selected from the group consisting of halogen;

with R10, R11, m, Y1, R50 and halogen as defined herein, also with all their embodiments.
Especially, COMPSUBST is selected from the group consisting of
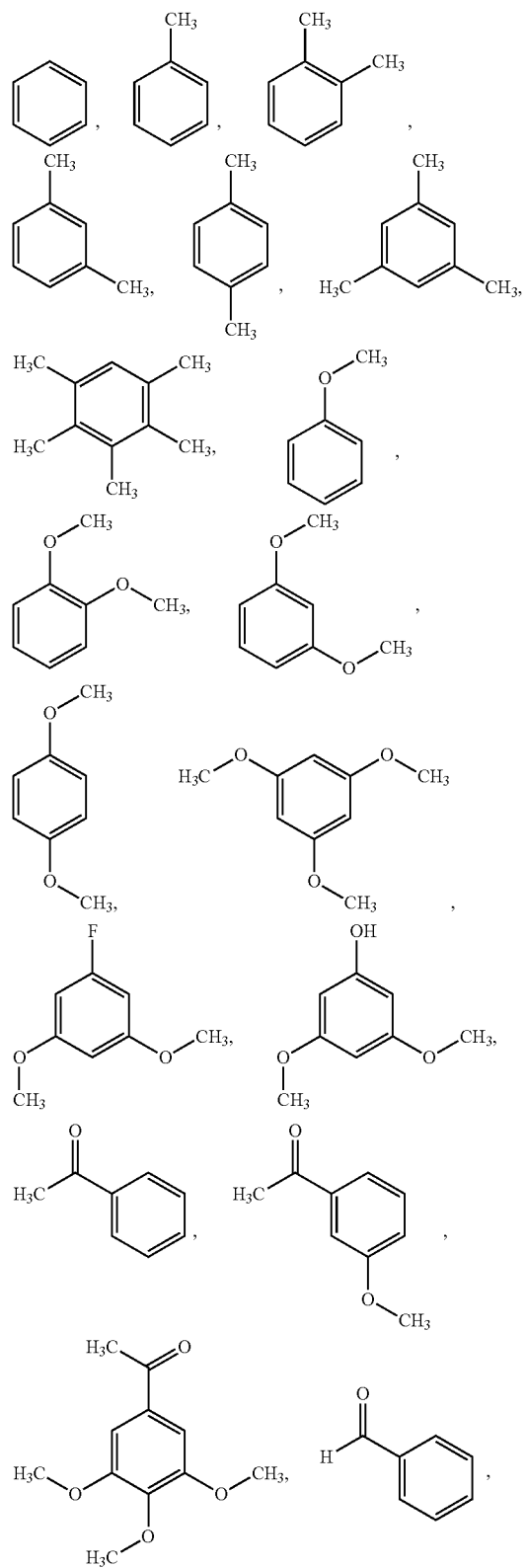

-continued

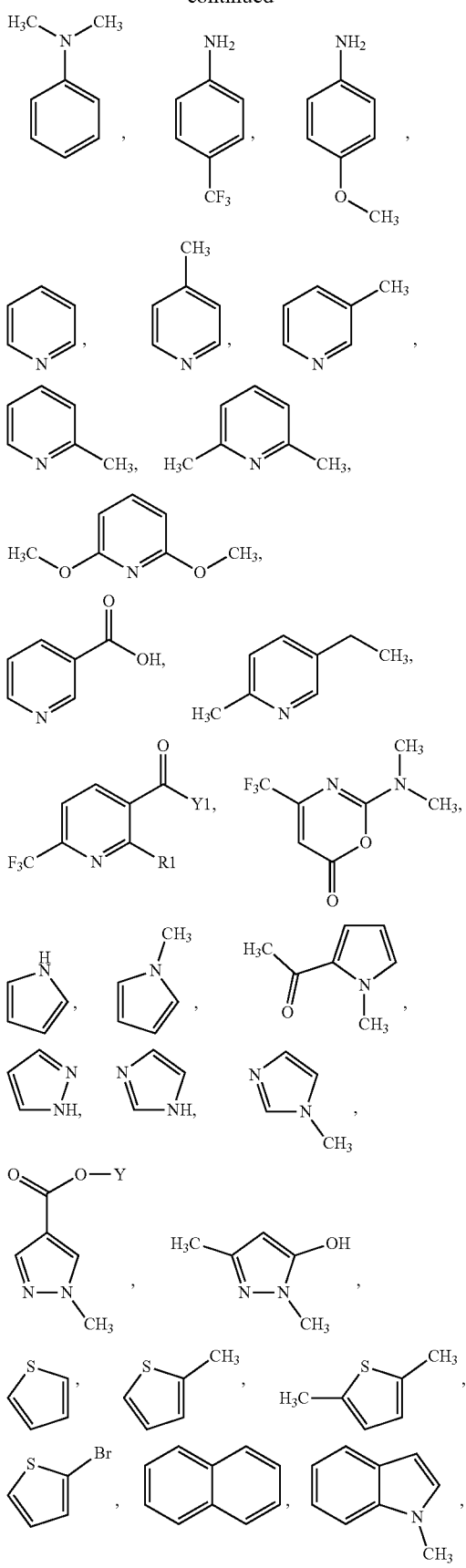

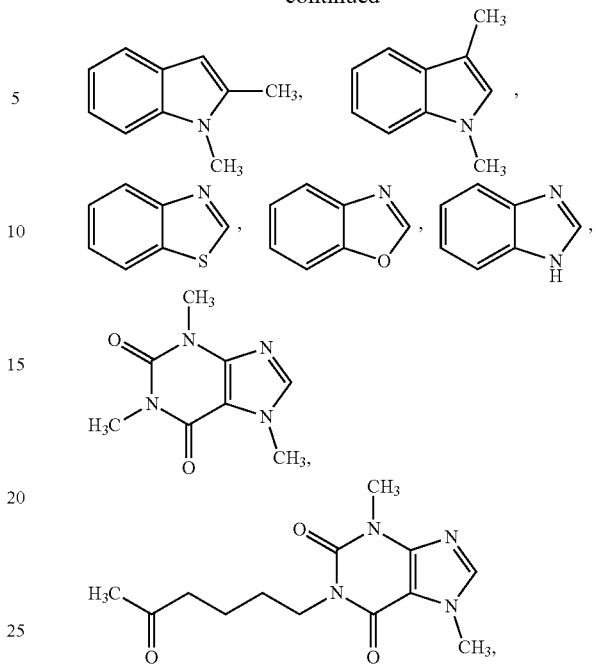

ethene, cyclohexene, ethine, and polystyrene;
Y is $C_{1-6}$ alkyl;
the ethene and the cyclohexene being unsubstituted or substituted by 1 or 2 substitutents selected from the group consisting of $C_{1-10}$ alkyl, $C_{1-4}$ alkoxy, N(R10)R11, CN, F, Cl, Br, I, $CF_3$, $(CH_2)_m$—C(O)Y1, benzyl, phenyl and morpholine;
the ethine being unsubstituted or substituted by 1 substitutent selected from the group consisting of $C_{1-10}$ alkyl, $C_{1-4}$ alkoxy, N(R10)R11, CN, F, Cl, Br, I, $CF_3$, $(CH_2)_m$—C(O)Y1, benzyl and phenyl;
with R10, R11, m and Y1 as defined herein, also with all their embodiments.

Preferably, Y is methyl or ethyl;
more preferably Y is ethyl.

Embodiments of the substituted ethene are propene, ethene-1,1-diyldibenzene and 3,3-dimethylbut-1-ene: preferably 3,3 dimethylbut 1 ene.

An embodiment of substituted cyclohexene is 4-(cyclohex-1-en-1-yl)morpholine.

An embodiment of the substituted ethine is 1-octyne.

An embodiment of COMPSUBST is compound of formula (PYRAZ)

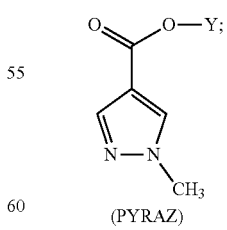

(PYRAZ)

wherein
Y is methyl or ethyl;
preferably Y is ethyl.

Preferably, R3 is CMS alkylen, wherein in the alkylen chain at least one of the hydrogens is substituted by F;

more preferably, R3 is $C_{1-10}$ alkylen, wherein in the alkylen chain at least one of the hydrogens is substituted by F.

Especially, FAHALIDE is selected from the group consisting of perfluoro $C_{1-20}$ alkyl-X1, Br—$(CF_2)_{n3}$—Br, and $F_2HC$—X1;

more especially, FAHALIDE is selected from the group consisting of perfluoro CMS alkyl-X1, Br—$(CF_2)_{n3}$—Br or $F_2HC$—X1;

even more especially, FAHALIDE is selected from the group consisting of perfluoro $C_{1-10}$ alkyl-X1, Br—$(CF_2)_{n3}$—Br or $F_2HC$—X1;

with n3 being an integer of 2 to 10;

preferably, n3 is 2, 3, 4, 5, 6;

more preferably, n3 is 2, 4 or 6;

even more preferably, n3 is 4.

In particular, FAHALIDE is selected from the group consisting of $F_{21}C_{10}$—I, $F_{21}C_{10}$—Br, $F_{17}C_8$—I, $F_{17}C_8$—Br, $F_{13}C_6$—I, $F_{13}C_6$—Br, $F_9C_4$—I, $F_9C_4$—Br, $F_7C_3$—I, $F_7C_3$—Br, $F_3C$—I, $F_3C$—Br, Br—$(CF_2)_4$—Br, $F_2HC$—I, and $F_2HC$—Br;

more in particular, FAHALIDE is selected from the group consisting of $F_{21}C_{10}$—I, $F_{17}C_8$—I, $F_9C_4$—I, $F_7C_3$—I, $F_3C$—Br, and Br—$(CF_2)_4$—Br.

In one embodiment,

X1 is I;

X2 is H.

In one embodiment,

R3 is perfluoroalkylen.

Preferably, from 0.1 to 20 mol %, more preferably from 0.5 to 15 mol %, even more preferably from 0.5 to 10 mol %, especially from 0.5 to 7.5 mol %, more especially from 0.5 to 6 mol %, even more especially from 0.75 to 5.5 mol %, of NICAT are used in the reaction, the mol % are based on the molar amount of FAHALIDE.

Preferably, from 0.1 to 20 mol %, more preferably from 0.5 to 15 mol %, even more preferably from 1 to 12.5 mol %, especially from 2 to 12.5 mol %, of LIG are used in the reaction, the mol % are based on the molar amount of FAHALIDE.

In case of FAHALIDE being in gaseous form at ambient temperature, then preferably FAHALIDE is used in the reaction in an amount which corresponds to a pressure of from 1 to 20 bar, more preferably from 1 to 15 bar, even more preferably from 1 to 10 bar, especially from 2 to 10 bar, more especially from 3 to 8 bar, even more especially from 4 to 8 bar, at ambient temperature.

Preferably, from 1 to 20 mol equivalents, more preferably 1 to 15 mol equivalents, even more preferably from 2 to 15 mol equivalents, especially from 2 to 12.5 mol equivalents, more especially from 2 to 11 mol equivalents, even more especially from 2.5 to 11 mol equivalents, of COMPSUBST are used in the reaction, the mol equivalents are based on the molar amount of FAHALIDE.

Preferably, from 0.1 to 10 mol equivalents, more preferably from 0.5 to 5 mol equivalents, even more preferably from 0.75 to 5 mol equivalents, especially from 0.85 to 5 mol equivalents, more especially from 0.95 to 5 mol equivalents, even more especially from 0.95 to 4 mol equivalents, in particular from 0.95 to 3 mol equivalents, of BAS are used in the reaction, the mol equivalents are based on the molar amount of FAHALIDE.

The reaction temperature of the reaction is preferably from 20 to 200° C., more preferably from 30 to 175° C., even more preferably from 40 to 175° C., especially from 40 to 150° C.

The reaction time of the reaction is preferably from 1 to 96 h, more preferably from 2 to 84 h, even more preferably from 3 to 80 h, especially from 4 to 76 h.

Preferably, the reaction is done under inert atmosphere. Preferably, the inert atmosphere is achieved by the use if an inert gas preferably selected from the group consisting of argon, another noble gas, lower boiling alkane, nitrogen, more preferably nitrogen.

The lower boiling alkane is preferably a $C_{1-3}$ alkane, i.e. methane, ethane or propane.

The reaction can be done in a closed system, it can be done at a pressure caused by the reaction mixture at the chosen temperature in a closed system, and/or caused by the pressure applied by COMPSUBST, in case that COMPSUBST is in gaseous form. It is also possible to apply pressure with said inert gas. It is also possible to carry out the reaction at ambient pressure.

The reaction can be done in the presence of a an additive ADD;

ADD is selected from the group consisting of Zn, polymethylhydrosiloxane, and phenylboronic acid.

Preferably, from 1 to 40 mol %, more preferably from 1 to 30 mol %, even more preferably from 1.5 to 30 mol %, especially from 1.5 to 25 mol %, more especially from 2 to 25 mol %, of ADD are used in the reaction, the mol % are based on the molar amount of FAHALIDE.

The reaction can be done in the presence of a an drying agent DRYAG;

DRYAG is selected from the group consisting of molecular sieve and $Na_2SO_4$;

preferably, the molecular sieve has a pore size of 4 angstrom.

The molecular sieve is preferably a $Na_{12}[(AlO_2)_{12}(SiO_2)_{12}] \times H_2O$.

Preferably, the amount of DRYAG used in the reaction is from 0.1 to 2 fold, more preferably from 0.1 to 1.5 fold, even more preferably from 0.1 to 1 fold, especially from 0.1 to 0.75 fold, more especially from 0.1 to 0.5 fold, based on the weight of FAHALIDE.

Preferably, the reaction can be done in the presence of DRYAG when NICAT is Ni-cat1.

The reaction can be done neat or in a solvent SOL, SOL is preferably selected from the group consisting of alkanes, chlorinated alkanes, ketones, ethers, esters, aliphatic nitrils, aliphatic amides, sulfoxides, $C_6F_6$, and mixtures thereof;

preferably SOL is selected from the group consisting of $C_{5-8}$ alkane, chlorinated $C_{5-8}$ alkane, acetone, methylethylketone, diethylketone, MTBE, tetrahydrofuran, methyltetrahydrofuran, ethylacetate, butylacetate, valeronitril, acetonitrile, dimethylformamide, dimethylacetamide, N-methylpyrrolidone, dimethylsulfoxide, $C_6F_6$, and mixtures thereof;

more preferably SOL is selected from the group consisting of acetone, methylethylketone, diethylketone, valeronitril, acetonitrile, dimethylsulfoxide, $C_6F_6$, and mixtures thereof;

even more preferably SOL is selected from the group consisting of acetone, methylethylketone, diethylketone, dimethylsulfoxide, $C_6F_6$, and mixtures thereof; especially SOL is $C_6F_6$.

It is also possible to use COMPSUBST and/or FAHALIDE simultaneously as solvent, meaning that the reaction is done neat.

Preferably, the reaction is done neat or in $C_6F_6$ as SOL.

The amount of SOL is preferably from 0.1 to 100 fold, more preferably from 1 to 50 fold, even more preferably from 1 to 25 fold, especially from 1 to 12.5 fold, more especially from 1 to 10 fold, even more especially from 3 to 10 fold, of the weight of FAHALIDE.

After the reaction, FACOMPSUBST can be isolated by standard methods such as evaporation of volatile components, extraction, washing, drying, concentration, crystallization, chromatography and any combination thereof, which are known per se to the person skilled in the art.

EXAMPLE

Abbreviations

4A-MS 4 Angström Molecular sieve, 70955-01-0, $Na_{12}[(AlO_2)_{12}(SiO_2)_{12}] \times H_2O$
Conv Conversion in mol % with regard to COMPSUBST
Sel Selectivity in mol % with regard to COMPSUBST
Ex Example
$Ni(NO_3)_2$ was used as $Ni(NO_3)_2 \cdot 6H_2O$
Proc Procedure
T reaction temperature
t reaction time General Procedure 1: Ni-Salt and Reduction Additives A mixture of COMPSUBST, FAHALIDE, NICAT, LIG, BAS, ADD, DRYAG, solvent (all equivalents and amounts are specified in the experimental table) were placed in a thick-walled pressure tube (Ace pressure tube, Sigma-Aldrich Art. Nr. Z564575). The gas atmosphere in the pressure tube was flushed with nitrogen, the tube was closed with a screw cap and heated (reaction temperature and reaction time are specified in Table 3). The resulting mixture was cooled to room temperature and diluted with dichloromethane (4 ml). The solids were removed by centrifugation (3000 rpm, 15 min). The obtained product solution was analyzed by quantitative GC analysis (internal standard hexadecane), $^{19}$F-NMR analysis using the internal standards 1,2-difluorobenzene or 1,4-difluorobenzene, or GC-MS.

Isolation of the products was conducted by pipette column chromatography using FluoroFlash® reverse phase silica gel (Sigma Aldrich No.: 00866) and a gradient solvent elution (1. MeOH:$H_2O$ (4:1. 10 mL) 2. MeOH (100%, 10 mL) 3. acetone (100%, 10 mL) for long chains perfluoroalkyl chains (alkyl chain containing 10 or more carbon atoms) or by normal phase silical gel chromatography using silicagel (Sigma Aldrich No.: 236802) and a gradient solvent elution (1. Pentane Ether (100%) 2. Pentane:Diethylether (50%:50%, 10 ml) for perfluoroalkyl chains containing less than 10 carbon atoms.

Procedure "Preformation of Ni-Cat2"

Preformation of Ni-cat2 was done according to Standley, E. A. et al., A Broadly Applicable Strategy for Entry into Homogeneous Nickel(0) Catalysts from Air-Stable Nickel (II) Complexes, Organometallics 2014, 33, 2012:

$NiCl_2 \cdot 6H_2O$ (8.5 mmol, 2.02 g) and EtOH (25 mL) were placed in an argon flushed round bottom flask equipped with a septum and a reflux condenser (Schlenk-flask). Then dppf (8.5 mmol, 4.712 g) was added and the resulting reaction mixture refluxed for 30 min (temperature ca. 80° C.), before cooled to 0° C. for 10 min. The so formed solid was collected by filtration and washed twice with EtOH (2 times with 10 mL) and with diethylether (2 times with 10 mL). After drying of the solid under vacuum (ca. 20 mbar, room temperature) 4.98 g intermediate Ni-int1, (dppf)$NiCl_2$, corresponding to 85% yield was obtained as a deep green powder.

This Ni-int1 (6.81 mmol, 4.658 g) and 180 mL $CH_2Cl_2$ were placed in an argon flushed round bottom flask. The resulting solution was cooled to 0° C., then o-tolylmagnesium chloride (6.81 mmol, 0.945 M in THF, 7.21 mL) was added dropwise with vigorous stirring. Near the end of the addition, the color of the solution changed from green to orange. This solution was stirred for an additional 15 min at 0° C. after addition, then the solvent was evaporated under vacuum at room temperature. Then 25 ml MeOH were added and the reaction mixture was stirred for 5 min at room temperature. After cooling this mixture to 0° C., the solid was collected by filtration, the residue was washed with MeOH (2 times with 5 ml) and dried under vacuum (ca. 5 mbar) at room temperature to yield 4.63 g Ni-cat2, (dppf)Ni(o-tol)Cl, corresponding to 92% yield as a fine, bright yellow powder.

$^1$H NMR (400 MHz, CD2Cl2): delta=8.23-8.12 (m, 4H), 8.02-7.93 (m, 2H), 7.51-7.38 (m, 7H), 7.27 (td, J=8.3, 2.0 Hz, 2H), 7.21-7.15 (m, 1H), 6.99 (t, J=7.4 Hz, 1H), 6.76 (td, J=8.2, 2.6 Hz, 2H), 6.66-6.54 (t, 2H), 6.43 (t, J=7.4 Hz, 1H), 6.30 (t, J=6.8 Hz, 1H), 6.10 (d, J=7.1 Hz, 1H), 5.15 (s, 1H), 4.54 (m, 1H), 4.25 (s, 1H), 4.19 (s, 1H), 4.02 (d, J=10.1 Hz, 2H), 3.52 (m, 1H), 3.33 (m, 1H), 2.44 (s, 3H).

$^{31}$P NMR (162 MHz, $CD_2Cl_2$): delta=29.51 (d, J=25.9 Hz, 1P), 12.12 (d, J=25.9 Hz, 1P).

General Procedure 2: Fluoroalkylation Using Preformed Ni-Cat2

A mixture of FAHALIDE (1 eq, 0.2 mmol), Ni-cat2 (5 mol %, 0.01 mmol, 7.40 mg, prepared according to the procedure "Preformation of Ni-cat2"), COMPSUBST (10 eq, 2 mmol,) and BAS were placed in a thick-walled Ace pressure tube (Sigma-Aldrich Art. Nr. Z564575). The gas atmosphere in the pressure tube was flushed with nitrogen, the tube was closed with a screw cap and heated for the reaction time and at the reaction temperature specified in the tables. The resulting reaction mixture was cooled to room temperature and diluted with dichloromethane (4 ml).

The solids were removed by centrifugation (3000 rpm, 15 min). The obtained product solution was analyzed by quantitative $^{19}$F-NMR analysis using 1,4-difluorobenzene or 1,2- difluorobenzene as internal standard, quantitative GC analysis using hexadecane as internal standard, or GC-MS.

Isolation of the products was conducted by pipette column chromatography using FluoroFlash® reverse phase silica gel (Sigma Aldrich No.: 00866) and a gradient solvent elution (1. MeOH:H$_2$O (4:1. 10 mL) 2. MeOH (100%, 10 mL) 3. acetone (100%, 10 mL) for long chains perfluoroalkyl chains (alkyl chain containing 10 or more carbon atoms) or by normal phase silical gel chromatography using silicagel (Sigma Aldrich No.: 236802) and a gradient solvent elution (1. Pentane Ether (100%) 2. Pentane:Diethylether (50%:50%, 10 ml) for perfluoroalkyl chains containing less than 10 carbon atoms.

Details of the examples are given in Tables 1, 2 and 3.

TABLE 1

| Ex | Proc | COMPSUBST | FAHALIDE | Product |
|---|---|---|---|---|
| 1 | 1 | 2-CF$_3$-aniline | (CF$_3$)$_2$CFI | 4-[(CF$_3$)$_2$CF]-2-CF$_3$-aniline |
| 2 | 2 | 2-CF$_3$-aniline | (CF$_3$)$_2$CFI | 4-[(CF$_3$)$_2$CF]-2-CF$_3$-aniline |
| 3 | 1 | 2-CF$_3$-aniline | (CF$_3$)$_2$CFI | 4-[(CF$_3$)$_2$CF]-2-CF$_3$-aniline |
| 4 | 1 | 2-CF$_3$-aniline | (CF$_3$)$_2$CFI | 4-[(CF$_3$)$_2$CF]-2-CF$_3$-aniline |
| 5 | 1 | 2-CF$_3$-aniline | (CF$_3$)$_2$CFI | 4-[(CF$_3$)$_2$CF]-2-CF$_3$-aniline |
| 6 | 1 | 2-CF$_3$-aniline | (CF$_3$)$_2$CFI | 4-[(CF$_3$)$_2$CF]-2-CF$_3$-aniline |
| 7 | 1 | 2-CF$_3$-aniline | (CF$_3$)$_2$CFI | 4-[(CF$_3$)$_2$CF]-2-CF$_3$-aniline |
| 8 | 1 | 2-CF$_3$-bromobenzene | (CF$_3$)$_2$CFI | 4-[(CF$_3$)$_2$CF]-2-CF$_3$-bromobenzene |

TABLE 1-continued

| Ex | Proc | COMPSUBST | FAHALIDE | Product |
|---|---|---|---|---|
| 9 | 1 | 2-(trifluoromethyl)aniline | (CF$_3$)$_2$CFI | 4-(perfluoroisopropyl)-2-(trifluoromethyl)aniline |
| 10 | 2 | benzene | C$_{10}$F$_{21}$I | (perfluorodecyl)benzene |
| 11 | 2 | anisole | C$_{10}$F$_{21}$I | (perfluorodecyl)anisole (mixture of isomers) |
| 12 | 2 | benzaldehyde | C$_{10}$F$_{21}$I | (perfluorodecyl)benzaldehyde (mixture of isomers) |
| 13 | 2 | 1,3-dimethoxybenzene | C$_{10}$F$_{21}$I | 1-(perfluorodecyl)-2,4-dimethoxybenzene |
| 14 | 2 | 1,3,5-trimethoxybenzene | C$_{10}$F$_{21}$I | 1-(perfluorodecyl)-2,4,6-trimethoxybenzene |
| 15 | 2 | 1-fluoro-3,5-dimethoxybenzene | C$_{10}$F$_{21}$I | 2-fluoro-4-(perfluorodecyl)-... |
| 16 | 2 | 1,2-dimethoxybenzene | C$_{10}$F$_{21}$I | 4-(perfluorodecyl)-1,2-dimethoxybenzene |
| 17 | 2 | 1,2-dimethylbenzene | C$_{10}$F$_{21}$I | 4-(perfluorodecyl)-1,2-dimethylbenzene |
| 18 | 2 | 1,4-dimethoxybenzene | C$_{10}$F$_{21}$I | 2-(perfluorodecyl)-1,4-dimethoxybenzene |
| 19 | 2 | N,N-diethylaniline | C$_{10}$F$_{21}$I | 4-(perfluorodecyl)-N,N-diethylaniline |

TABLE 1-continued

| Ex | Proc | COMPSUBST | FAHALIDE | Product |
|---|---|---|---|---|
| 20 | 2 | 2,4-dimethylaniline | $C_{10}F_{21}I$ | 6-$C_{10}F_{21}$-2,4-dimethylaniline (position 6, methyls at 3) |
| 21 | 2 | 2,6-dimethylaniline | $C_{10}F_{21}I$ | 4-$C_{10}F_{21}$-2,6-dimethylaniline |
| 22 | 2 | 4-fluoroaniline | $C_{10}F_{21}I$ | 4-fluoro-2-$C_{10}F_{21}$-aniline |
| 23 | 2 | 4-methoxyaniline | $C_{10}F_{21}I$ | 2-$C_{10}F_{21}$-4-methoxyaniline |
| 24 | 2 | pyridine | $C_{10}F_{21}I$ | 2-$C_{10}F_{21}$-pyridine (positions 3, 4 labeled) |
| 25 | 2 | 2,6-dimethoxypyridine | $C_{10}F_{21}I$ | 3-$C_{10}F_{21}$-2,6-dimethoxypyridine |
| 26 | 2 | 1-methylpyrrole | $C_{10}F_{21}I$ | 3-$C_{10}F_{21}$-1-methylpyrrole |
| 27 | 2 | 2,5-dimethylthiophene | $C_{10}F_{21}I$ | 3-$C_{10}F_{21}$-2,5-dimethylthiophene |
| 28 | 2 | 1-methylimidazole | $C_{10}F_{21}I$ | 4-$C_{10}F_{21}$-1-methylimidazole (positions 2, 5 labeled) |
| 29 | 2 | naphthalene | $C_{10}F_{21}I$ | $C_{10}F_{21}$-naphthalene (positions 1, 2) |
| 30 | 2 | benzene | $C_8F_{17}I$ | $C_8F_{17}$-benzene |

TABLE 1-continued
| Ex | Proc | COMPSUBST | FAHALIDE | Product |
|---|---|---|---|---|
| 31 | 2 |  | C₄F₉I | 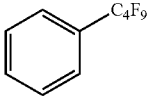 |
| 32 | 22 |  | 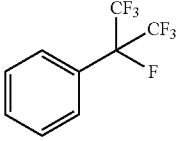 | 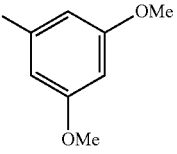 |
| 33 | 2 | 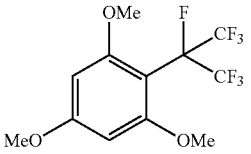 | 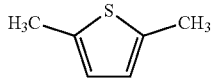 | 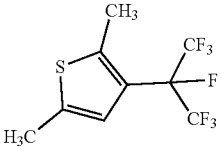 |
| 34 | 2 | 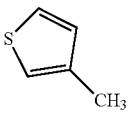 | 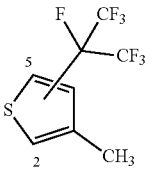 | 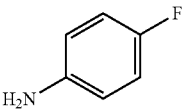 |
| 35 | 2 | 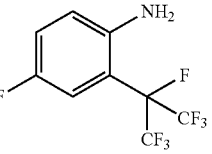 | 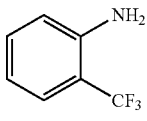 | 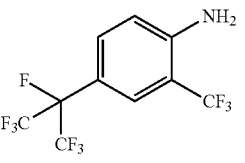 [SMILES: Nc1ccc(C(F)(C(F)(F)F)C(F)(F)F)cc1C(F)(F)F] |
| 36 | 2 | 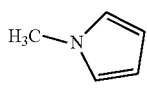 | 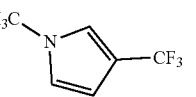 | 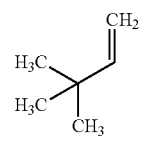 |
| 37 | 2 | 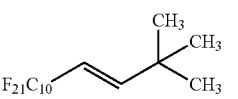 | | |
| 38 | 2 | | CF₃Br | |
| 39 | 2 | | C₁₀F₂₁I | |
| 40 | 2 | | C₄F₉I | 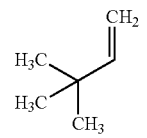 |
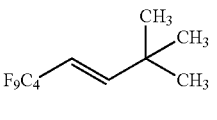

TABLE 1-continued

| Ex | Proc | COMPSUBST | FAHALIDE | Product |
|---|---|---|---|---|
| 41 | 2 | H₃C-C(CH₃)(CH₃)-CH=CH₂ | $C_8F_{17}I$ | $F_{17}C_8$-CH=CH-C(CH₃)(CH₃)(CH₃) |
| 42 | 2 | H₃C-C(CH₃)(CH₃)-CH=CH₂ | Br-CF₂-CF₂-CF₂-CF₂-Br | $BrF_8C_4$-CH=CH-C(CH₃)(CH₃)(CH₃) |
| 43 | 2 | H₃C-C(CH₃)(CH₃)-CH=CH₂ | (CF₃)₂CF-I with F | H₃C-C(CH₃)(CH₃)-CH=CH-C(CF₃)(CF₃)F |

TABLE 2

| Ex | Proc | COMPSUBST Amount | FAHALIDE Amount | NICAT | LIG | ADD | BAS |
|---|---|---|---|---|---|---|---|
| 1 | 1 | 0.5 ml<br>4 mmol | 0.5 mmol<br>150 mg<br>1 eq | NiCl₂(DME)<br>5 mol % | DPEPhos<br>10 mol % | — | Cs₂CO₃<br>1 eq |
| 2 | 2 | 0.5 ml<br>4 mmol | 0.5 mmol<br>150 mg<br>1 eq | Ni-cat2<br>5 mol % | — | — | Cs₂CO₃<br>1 eq |
| 3 | 1 | 0.25 ml<br>2 mmol | 0.5 mmol<br>150 mg<br>1 eq | NiCl₂(DME)<br>5 mol % | DPEPhos<br>10 mol % | — | Cs₂CO₃<br>1 eq |
| 4 | 1 | 0.25 ml<br>2 mmol | 0.5 mmol<br>150 mg<br>1 eq | NiCl₂(DME)<br>5 mol % | DPEPhos<br>10 mol % | — | K₃PO₄<br>1 eq |
| 5 | 1 | 0.3 ml<br>2.4 mmol | 0.5 mmol<br>150 mg<br>1 eq | Ni(NO₃)₂<br>5 mol % | DPEPhos<br>6 mol % | Zn<br>15 mol % | K₃PO₄<br>1 eq |
| 6 | 1 | 0.6 ml<br>4.8 mmol | 0.5 mmol<br>150 mg<br>1 eq | Ni(NO₃)₂<br>2.5 mol % | DPEPhos<br>3 mol % | Zn<br>2.5 mol % | K₃PO₄<br>1 eq |
| 7 | 1 | 0.3 ml<br>2.4 mmol | 0.5 mmol<br>150 mg<br>1 eq | Ni(NO₃)₂<br>3 mol % | DPEPhos<br>3 mol % | Zn<br>2.5 mol % | K₃PO₄<br>1 eq |
| 8 | 1 | 0.4 ml<br>3 mmol | 1 mmol<br>300 mg<br>1 eq | Ni(NO₃)₂<br>3 mol % | DPEPhos<br>3 mol % | Zn<br>5 mol % | K₃PO₄<br>1 eq |
| 9 | 1 | 0.2 ml<br>1.6 mmol | 0.5 mmol<br>150 mg<br>1 eq | Ni(NO₃)₂<br>3 mol % | Ph₃P<br>6 mol % | PHMS<br>20 mol % | K₃PO₄<br>1 eq |
| 10 | 2 | 0.5 ml | 0.2 mmol<br>130 mg<br>1 eq | Ni-cat2<br>5 mol % | — | — | Cs₂CO₃<br>1.5 eq |
| 11 | 2 | 0.5 ml | 0.2 mmol<br>130 mg<br>1 eq | Ni-cat2<br>5 mol % | — | — | Cs₂CO₃<br>1.5 eq |
| 12 | 2 | 0.5 ml | 0.2 mmol<br>130 mg<br>1 eq | Ni-cat2<br>5 mol % | — | — | Cs₂CO₃<br>1.5 eq |
| 13 | 2 | 0.5 ml | 0.2 mmol<br>130 mg<br>1 eq | Ni-cat2<br>5 mol % | — | — | Cs₂CO₃<br>1.5 eq |
| 14 | 2 | 0.5 ml | 0.2 mmol<br>130 mg<br>1 eq | Ni-cat2<br>5 mol % | — | — | Cs₂CO₃<br>1.5 eq |
| 15 | 2 | 0.5 ml | 0.2 mmol<br>130 mg<br>1 eq | Ni-cat2<br>5 mol % | — | — | Cs₂CO₃<br>1.5 eq |
| 16 | 2 | 0.5 ml | 0.2 mmol<br>130 mg<br>1 eq | Ni-cat2<br>5 mol % | — | — | Cs₂CO₃<br>1.5 eq |

TABLE 2-continued

| Ex | Proc | COMPSUBST Amount | FAHALIDE Amount | NICAT | LIG | ADD | BAS |
|---|---|---|---|---|---|---|---|
| 17 | 2 | 0.5 ml | 0.2 mmol<br>130 mg<br>1 eq | Ni-cat2<br>5 mol % | — | — | Cs₂CO₃<br>1.5 eq |
| 18 | 2 | 0.5 ml | 0.2 mmol<br>130 mg<br>1 eq | Ni-cat2<br>5 mol % | — | — | Cs₂CO₃<br>1.5 eq |
| 19 | 2 | 0.5 ml | 0.2 mmol<br>130 mg<br>1 eq | Ni-cat2<br>5 mol % | — | — | Cs₂CO₃<br>1.5 eq |
| 20 | 2 | 0.5 ml | 0.2 mmol<br>130 mg<br>1 eq | Ni-cat2<br>5 mol % | — | — | Cs₂CO₃<br>1.5 eq |
| 21 | 2 | 0.5 ml | 0.2 mmol<br>130 mg<br>1 eq | Ni-cat2<br>5 mol % | — | — | Cs₂CO₃<br>1.5 eq |
| 22 | 2 | 0.5 ml | 0.2 mmol<br>130 mg<br>1 eq | Ni-cat2<br>5 mol % | — | — | Cs₂CO₃<br>1.5 eq |
| 23 | 2 | 0.5 ml | 0.2 mmol<br>130 mg<br>1 eq | Ni-cat2<br>5 mol % | — | — | Cs₂CO₃<br>1.5 eq |
| 24 | 2 | 0.5 ml | 0.2 mmol<br>130 mg<br>1 eq | Ni-cat2<br>5 mol % | — | — | Cs₂CO₃<br>1.5 eq |
| 25 | 2 | 0.5 ml | 0.2 mmol<br>130 mg<br>1 eq | Ni-cat2<br>5 mol % | — | — | Cs₂CO₃<br>1.5 eq |
| 26 | 2 | 0.5 ml | 0.2 mmol<br>130 mg<br>1 eq | Ni-cat2<br>5 mol % | — | — | Cs₂CO₃<br>1.5 eq |
| 27 | 2 | 0.5 ml | 0.2 mmol<br>130 mg<br>1 eq | Ni-cat2<br>5 mol % | — | — | Cs₂CO₃<br>1.5 eq |
| 28 | 2 | 0.5 ml | 0.2 mmol<br>130 mg<br>1 eq | Ni-cat2<br>5 mol % | — | — | Cs₂CO₃<br>1.5 eq |
| 29 | 2 | 0.5 ml | 0.2 mmol<br>130 mg<br>1 eq | Ni-cat2<br>5 mol % | — | — | Cs₂CO₃<br>1.5 eq |
| 30 | 2 | 0.5 ml | 0.2 mmol<br>110 mg<br>1 eq | Ni-cat2<br>5 mol % | — | — | Cs₂CO₃<br>1.5 eq |
| 31 | 2 | 0.5 ml | 0.5 mmol<br>170 mg<br>1 eq | Ni-cat2<br>5 mol % | — | — | Cs₂CO₃<br>1.5 eq |
| 32 | 22 | 0.5 ml | 0.5 mmol<br>150 mg<br>1 eq | Ni-cat2<br>5 mol % | — | — | Cs₂CO₃<br>1.5 eq |
| 33 | 2 | 170 mg<br>1 mmol<br>2 eq | 0.5 mmol<br>150 mg<br>1 eq | Ni-cat2<br>5 mol % | — | — | Cs₂CO₃<br>1.5 eq |
| 34 | 2 | 0.5 ml | 0.5 mmol<br>150 mg<br>1 eq | Ni-cat2<br>5 mol % | — | — | Cs₂CO₃<br>1.5 eq |
| 35 | 2 | 0.5 ml | 0.5 mmol<br>150 mg<br>1 eq | Ni-cat2<br>5 mol % | — | — | Cs₂CO₃<br>1.5 eq |
| 36 | 2 | 111 mg<br>1 mmol<br>2 eq | 0.5 mmol<br>150 mg<br>1 eq | Ni-cat2<br>5 mol % | — | — | Cs₂CO₃<br>1.5 eq |
| 37 | 2 | 160 mg<br>1 mmol<br>2 eq | 0.5 mmol<br>150 mg<br>1 eq | Ni-cat2<br>5 mol % | — | — | Cs₂CO₃<br>1.5 eq |
| 38 | 2 | 0.5 mmol<br>40 mg<br>1 eq | 5 bar | Ni-cat2<br>5 mol % | — | PhB-acid<br>10 mol % | Cs₂CO₃<br>1.5 eq |
| 39 | 2 | 0.5 ml<br>325 mg<br>4 eq | 0.2 mmol<br>130 mg<br>1 eq | Ni-cat2<br>5 mol % | — | — | NaH<br>2 eq |
| 40 | 2 | 0.5 ml<br>325 mg<br>4 eq | 0.5 mmol<br>175 mg<br>1 eq | Ni-cat2<br>1 mol % | — | — | NaOtBu<br>2 eq |
| 41 | 2 | 0.5 ml<br>325 mg<br>4 eq | 0.5 mmol<br>275 mg<br>1 eq | Ni-cat2<br>1 mol % | — | — | NaOtBu<br>2 eq |

TABLE 2-continued

| Ex | Proc | COMPSUBST Amount | FAHALIDE Amount | NICAT | LIG | ADD | BAS |
|---|---|---|---|---|---|---|---|
| 42 | 2 | 0.5 ml<br>325 mg<br>4 eq | 0.5 mmol<br>180 mg<br>1 eq | Ni-cat2<br>1 mol % | — | — | NaOtBu<br>2 eq |
| 43 | 2 | 0.5 ml<br>325 mg<br>4 eq | 0.5 mmol<br>150 mg<br>1 eq | Ni-cat2<br>1 mol % | — | — | NaOtBu<br>2 eq |

TABLE 3

| Ex | Proc | DRYAG | Solvent | T | t | Conv | Sel | Yield | Remarks |
|---|---|---|---|---|---|---|---|---|---|
| 1 | 1 | 4A-MS 50 mg | neat | 50° C. | 20 h | 100% | 65% | 63% | o-isomer: +21%<br>GCMS<br>$^{19}$F-NMR |
| 2 | 2 | 4A-MS 50 mg | neat | 50° C. | 20 h | 97% | 65% | 63% | o-isomer: +21%<br>GCMS<br>$^{19}$F-NMR |
| 3 | 1 | 4A-MS 25 mg | neat | 50° C. | 24 h | 89% | 60% | 53% | o-isomer: +21%<br>5% PfP-H<br>GCMS<br>$^{19}$F-NMR |
| 4 | 1 | 4A-MS 25 mg | neat | 50° C. | 24 h | 65% | 55% | 36% | o-isomer: +15%<br>4% PfP-H<br>GCMS<br>$^{19}$F-NMR |
| 5 | 1 | 4A-MS 30mg | neat | 100° C. | 6 h | 98% | 73% | 72% | o-isomer: +17%<br>1% PfP-H<br>GCMS<br>$^{19}$F-NMR |
| 6 | 1 | 4A-MS 50 mg | neat | 100° C. | 72 h | 95% | 81% | 77% | o-isomer: +8%<br>GCMS<br>$^{19}$F-NMR |
| 7 | 1 | 4A-MS 25 mg | neat | 100° C. | 16 h | 84% | 85% | 71% | o-isomer: +5%<br>1% PfP-H<br>GCMS<br>$^{19}$F-NMR |
| 8 | 1 | 4A-MS 40 mg | neat | 100° C. | 16 h | 99% | 68% | 67% | o-isomer: +20%<br>1% PfP-H<br>GCMS<br>$^{19}$F-NMR |
| 9 | 1 | Na2SO4 25 mg | neat | 90° C. | 24 h | 98% | 72% | 71% | o-isomer: +4%<br>3% PfP-H<br>GCMS<br>$^{19}$F-NMR |
| 10 | 2 | — | neat | 100° C. | 16 h | 97% | 77% | 75% | $^{19}$F-NMR |
| 11 | 2 | — | neat | 130° C. | 16 h | | | 91% | 2-isomer: 35%<br>3-isomer: 15%<br>4-isomer: 40%<br>$^{19}$F-NMR |
| 12 | 2 | — | neat | 120° C. | 16 h | | | 55% | 2-isomer: 25%<br>3-isomer: 9%<br>4-isomer: 21%<br>$^{19}$F-NMR |
| 13 | 2 | | neat | 100° C. | 16 h | | | 86% | $^{19}$F-NMR |
| 14 | 2 | | neat | 100° C. | 16 h | | | 73% | $^{19}$F-NMR |
| 15 | 2 | | neat | 100° C. | 24 h | | | 73% | 2-isomer: 48%<br>4-isomer: 25%<br>$^{19}$F-NMR |
| 16 | 2 | | neat | 130° C. | 16 h | | | 54% | $^{19}$F-NMR |
| 17 | 2 | | neat | 130° C. | 17 h | | | 66% | 3-isomer: 18%<br>4-isomer: 48%<br>$^{19}$F-NMR |
| 18 | 2 | | neat | 120° C. | 16 h | | | 78% | $^{19}$F-NMR |
| 19 | 2 | | neat | 100° C. | 16 h | | | 70% | 2-isomer: 19%<br>4-isomer: 51%<br>$^{19}$F-NMR |
| 20 | 2 | | neat | 100° C. | 16 h | | | 95% | 3-isomer: 19%<br>6-isomer: 51%<br>$^{19}$F-NMR |
| 21 | 2 | | neat | 100° C. | 30 h | | | 96% | 3-isomer: 10%<br>4-isomer: 86%<br>$^{19}$F-NMR |
| 22 | 2 | | neat | 120° C. | 24 h | | | 74% | $^{19}$F-NMR |
| 23 | 2 | | neat | 130° C. | 16 h | | | 73% | $^{19}$F-NMR |

TABLE 3-continued

| Ex | Proc | DRYAG | Solvent | T | t | Conv | Sel | Yield | Remarks |
|---|---|---|---|---|---|---|---|---|---|
| 24 | 2 | | neat | 130° C. | 26 h | | | 59% | 2-isomer: 26%<br>3-isomer: 5%<br>4-isomer: 28%<br>$^{19}$F-NMR |
| 25 | 2 | — | neat | 130° C. | 16 h | | | 96% | $^{19}$F-NMR |
| 26 | 2 | — | neat | 80° C. | 16 h | | | 86% | $^{19}$F-NMR |
| 27 | 2 | — | neat | 120° C. | 16 h | | | 55% | $^{19}$F-NMR |
| 28 | 2 | — | neat | 130° C. | 17 h | | | 61% | 2-isomer: 23%<br>4-isomer: 17%<br>5-isomer: 21%<br>$^{19}$F-NMR |
| 29 | 2 | — | neat | 130° C. | 26 h | | | 51% | 1-isomer: 40%<br>2-isomer: 11%<br>$^{19}$F-NMR |
| 30 | 2 | — | neat | 120° C. | 16 h | | | 76% | $^{19}$F-NMR |
| 31 | 2 | — | neat | 120° C. | 22 h | | | 50% | $^{19}$F-NMR |
| 32 | 22 | — | neat | 100° C. | 16 h | | | 54% | $^{19}$F-NMR |
| 33 | 2 | — | $C_6F_6$ 0.5 ml | 100° C. | 16 h | | | 52% | $^{19}$F-NMR |
| 34 | 2 | — | neat | 100° C. | 16 h | | | 60% | $^{19}$F-NMR |
| 35 | 2 | — | neat | 100° C. | 16 h | | | 80% | 2-isomer: 41%<br>5-isomer: 39%<br>$^{19}$F-NMR |
| 36 | 2 | — | $C_6F_6$ 0.5 ml | 100° C. | 16 h | | | 80% | $^{19}$F-NMR |
| 37 | 2 | — | $C_6F_6$ 0.5 ml | 100° C. | 16 h | | | 85% | $^{19}$F-NMR |
| 38 | 2 | — | $C_6F_6$ 1 ml | 100° C. | 16 h | | | 72% | $^{19}$F-NMR |
| 39 | 2 | — | neat | 80° C. | 16 h | 100% | 64% | 64% | $^{19}$F-NMR |
| 40 | 2 | — | neat | 50° C. | 16 h | | | 73% | $^{19}$F-NMR |
| 41 | 2 | — | neat | 50° C. | 16 h | | | 89% | $^{19}$F-NMR |
| 42 | 2 | — | neat | 50° C. | 16 h | | | 69% | $^{19}$F-NMR |
| 43 | 2 | — | neat | 50° C. | 16 h | | | 61% | $^{19}$F-NMR |

Comparative Example

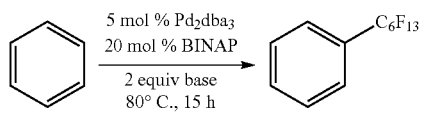

The entry 10 in Table 1 of Loy, R. N., et al., Organic Letters 2011, 13, 2548-2551, was repeated according to the detailed procedure given in the Supporting Information for said article, which is described under "Optimization procedure" on page S3 in connection with entry 9 in Table S4 on page S5.
The phosphine was BINAP.
[Pd] was $Pd_2dba_3$.
The base was $Cs_2CO_3$.
The alkylhalogenid was perfluorohexyl bromide instead of perfluorohexyl iodide.
To a screw cap 1 dram vial was added base (0.4 mmol, 2 equiv), [Pd] (0.02 mmol, 10 mol %) and phosphine (0.04-0.08 mmol, 20-40 mol %). Benzene (1 mL) and perfluorohexyl bromide (43 microL, 0.2 mmol, 1 equiv) were added, and the resulting mixture was sealed with a Teflon-lined cap and heated in an aluminum reaction block with vigorous stirring for 15 h at 80° C. The reaction mixture was cooled to 23° C. and chlorobenzene (20 microL) was added as a GC internal standard. An aliquot (ca. 100 microL) was removed from the crude reaction mixture and passed through a plug of Celite, eluting with EtOAc (2 mL). This sample was then analyzed by GC, and the yield was determined by comparison to a calibration against the chlorobenzene internal standard.

Result:
A yield of less than 1% was measured.

The invention claimed is:
1. A method for preparation of a mono-fluoro alkylated compound FACOMPSUBST that is mono-fluoroalkylated at a sp2 carbon, by a reaction of a compound COMPSUBST with a fluoro alkyl halide FAHALIDE by homogeneous catalysis using a Ni catalyst NICAT in the presence of a base BAS;
wherein
NICAT is Ni-cat1 or Ni-cat2;
Ni-cat1 is a combination of a nickel salt NISALT with a ligand LIG
NISALT is $NiCl_2$ or $Ni(NO_3)_2$;
LIG is selected from the group consisting of compound of formula (DPEPhos), compound of formula (dppb) and $Ph_3P$;

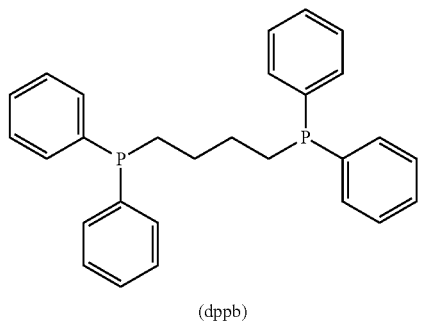

(dppb)

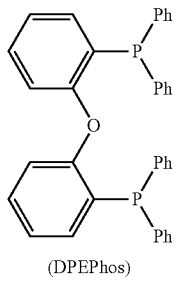

(DPEPhos)

Ni-cat2 is compound of formula (Ni-cat2);

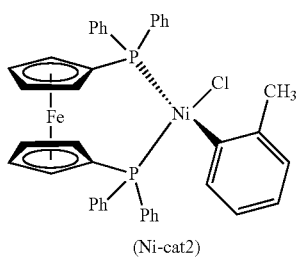

(Ni-cat2)

BAS is selected from the group consisting of $Cs_2CO_3$, $CsHCO_3$, $K_3PO_4$, NaH and NaOtBu;

FAHALIDE is selected from the group consisting of perfluoro $C_{1-20}$ alkyl-X1, and Br—$(CF_2)_{n3}$—Br;
wherein X1 is Br or I;
with n3 being an integer of 2 to 10;

COMPSUBST is selected from the group consisting of a compound COMPSUBST-I, ethene, and polystyrene;
the ethene being substituted by 1 substituent selected from the group consisting of $C_{1-10}$ alkyl;
COMPSUBST-I is a compound of formula (COMPSUBST-I);

RINGA(COMPSUBST-I)

RINGA is a 5 or 6 membered carbocyclic or heterocyclic ring,
when RINGA is a heterocyclic ring, then RINGA has 1, 2 or 3 identical or different endocyclic heteroatoms independently from each other selected from the group consisting of N, O and S,
when RINGA is a 5 membered ring, then RINGA is unsubstituted or substituted by 1, 2, 3 or 4 identical or different substituents,
when RINGA is a 6 membered ring then RINGA is unsubstituted or substituted by 1, 2, 3, 4 or 5 identical or different substituents,
any of the substituents of RINGA is independently from any other of the substituents of RINGA selected from the group consisting of $C_{1-10}$ alkyl, $C_{3-8}$ cycloalkyl, $C_{1-4}$ alkoxy, OH, N(R10)R11, CN, NH—OH, NO, $NO_2$, F, Cl, Br, I, $CF_3$, $(CH_2)_m$—C(O)Y1, $S(O)_2R50$, CH=C(H)R28, C≡C—R24, benzyl, phenyl and naphthyl;

RINGA can be condensed with a ring RINGB, RINGB is a 5 or 6 membered carbocyclic or heterocyclic ring,
when RINGB is a heterocyclic ring, is contains 1, 2 or 3 identical or different endocyclic heteroatoms independently from each other selected from the group consisting of N, O and S;

when RINGB is a 5 membered ring, then RINGB is unsubstituted or substituted by 1, 2 or 3 identical or different substituents,
when RINGB is a 6 membered ring then RINGB is unsubstituted or substituted by 1, 2, 3 or 4 identical or different substituents,
any of the substituents of RINGB is independently from any other of the substituents of RINGB selected from the group consisting of $C_{1-10}$ alkyl, $C_{3-8}$ cycloalkyl, $C_{1-4}$ alkoxy, OH, N(R17)R18, CN, NH—OH, NO, $NO_2$, F, Cl, Br, I, $CF_3$, $(CH_2)_n$—C(O)Y2, $S(O)_2R51$, CH=C(H)R38, C≡C—R34, benzyl, phenyl and naphthyl;
any of the $C_{1-10}$ alkyl substituent of RINGA or RINGB is unsubstituted or substituted with 1, 2, 3, 4 or 5 identical or different substituents selected from the group consisting of halogen, OH, O—C(O)—$C_{1-5}$ alkyl, O—$C_{1-10}$ alkyl, S—$C_{1-10}$ alkyl, S(O)—$C_{1-10}$ alkyl, $S(O_2)$—$C_{1-10}$ alkyl, O—$C_{1-6}$ alkylen-O—$C_{1-6}$ alkyl, $C_{3-8}$ cycloalkyl and 1,2,4-triazolyl;
any of said benzyl, phenyl and naphthyl substituent of RINGA or RINGB is independently from each other unsubstituted or substituted with 1, 2, 3, 4 or 5 identical or different substituents selected from the group consisting of halogen, $C_{1-4}$ alkoxy, $NO_2$ and CN;
m and n are identical or different and independently from each other 0, 1, 2, 3, 4, 5, 6, 7, 8, 9 or 10;
Y1 and Y2 are identical or different and independently from each other selected from the group consisting of H, OH, C(R14)(R15)R16, $C_{1-6}$ alkyl, O—$C_{1-6}$ alkyl, phenyl, benzyl, O-phenyl, O—$C_{1-6}$ alkylen-O—$C_{1-6}$ alkyl and N(R19)R20;
R14, R15 and R16 are identical or different and independently from each other selected from the group consisting of H, F, Cl and Br;
R10, R11, R17, R18, R19 and R20 are identical or different and are independently from each other H or $C_{1-6}$ alkyl, or R10 and R11, R17 and R18 or R19 and R20 represent together a tetramethylene or a pentamethylene chain;
R50 and R51 are identical or different and independently from each other selected from the group consisting of OH, $C_{1-6}$ alkyl and $C_{1-6}$ alkoxy;
R24, R34, R28 and R38 are identical or different and independently from each other selected from the group consisting of H, $C_{1-10}$ alkyl, C(R25)(R26)-O—R27;
R25, R26 and R27 are identical or different and independently from each other selected from the group consisting of H and $C_{1-10}$ alkyl; and
wherein if COMPSUBST is ethene as defined above, FACOMPSUBST is a 1,2-disubstituted ethene.

2. The method according to claim 1, wherein
LIG is compound of formula (DPEPhos) or $Ph_3P$.

3. The method according to claim 1, wherein
BAS is selected from the group consisting of $Cs_2CO_3$, $K_3PO_4$, NaH and NaOtBu.

4. The method according to claim 1, wherein
COMPSUBST is selected from the group consisting of compound COMPSUBST-I, ethene, and polystyrene;
the ethene being substituted by 1 substituent selected from the group consisting of $C_{1-10}$ alkyl;
with COMPSUBST-I being selected from the group consisting of

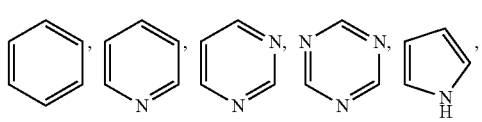

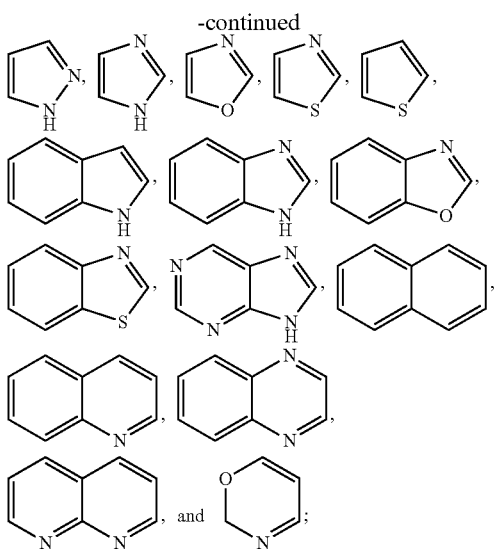

with COMPSUBST-I being unsubstituted or substituted
by 1, 2, 3 or 4 in case of COMPSUBST-I being a monocyclic compound with 5 endocyclic atoms,
by 1, 2, 3, 4 or 5 in case of COMPSUBST-I being a monocyclic compound with 6 endocyclic atoms,
by 1, 2, 3, 4, 5 or 6 in case of COMPSUBST-I being a bicyclic compound wherein a 5-membered and a 6-membered ring are ortho-fused,
by 1, 2, 3, 4, 5, 6 or 7 in case of COMPSUBST-I being a bicyclic compound wherein two 6-membered rings are ortho-fused,
identical or different substituents independently from each other selected from the group consisting of $C_{1-10}$ alkyl, $C_{3-8}$ cycloalkyl, $C_{1-4}$ alkoxy, OH, C(H)=O, N(R10)R11, CN, NH—OH, NO, $NO_2$, F, Cl, Br, I, $CF_3$, $(CH_2)_m$—C(O)Y1, $S(O)_2R50$, CH=C(H)R28, C≡C—R24, benzyl, phenyl and naphthyl;
said $C_{1-10}$ alkyl substituent of COMPSUBST-I is unsubstituted or substituted with 1, 2, 3, 4 or 5 identical or different substituents selected from the group consisting of halogen, OH, O—C(O)—$C_{1-5}$ alkyl, O—$C_{1-10}$ alkyl, S—$C_{1-10}$ alkyl, S(O)—$C_{1-10}$ alkyl, $S(O_2)$—$C_{1-10}$ alkyl, O—$C_{1-6}$ alkylen-O—$C_{1-6}$ alkyl, $C_{3-8}$ cycloalkyl and 1,2,4-triazolyl;
said benzyl, phenyl and naphthyl substituents of COMPSUBST-I are independently from each other unsubstituted or substituted with 1, 2, 3, 4 or 5 identical or different substituents selected from the group consisting of halogen, $C_{1-4}$ alkoxy, $NO_2$ and CN.

5. The method according to claim 1, wherein
COMPSUBST-I is unsubstituted or substituted
by 1, 2 or 3 in case of COMPSUBST-I being a monocyclic compound with 5 endocyclic atoms,
by 1, 2, 3, 4 or 5 in case of COMPSUBST-I being a monocyclic compound with 6 endocyclic atoms,
by 1, 2, 3 or 4 in case of COMPSUBST-I being a bicyclic compound wherein a 5-membered and a 6-membered ring are ortho-fused,
by 1, 2, 3, 4 or 5 in case of COMPSUBST-I being a bicyclic compound wherein two 6-membered rings are ortho-fused,
identical or different substituents independently from each other selected from the group consisting of $C_{1-4}$ alkyl, $C_{1-4}$ alkoxy, OH, C(H)=O, N(R10)R11, CN, F, Cl, Br, $CF_3$, $(CH_2)_m$—C(O)Y1, and $S(O)_2R50$;
said $C_{1-4}$ alkyl substituent of COMPSUBST-I is unsubstituted or substituted with 1, 2 or 3 identical or different substituents selected from the group consisting of halogen.

6. The method according to claim 1, wherein
COMPSUBST is selected from the group consisting of

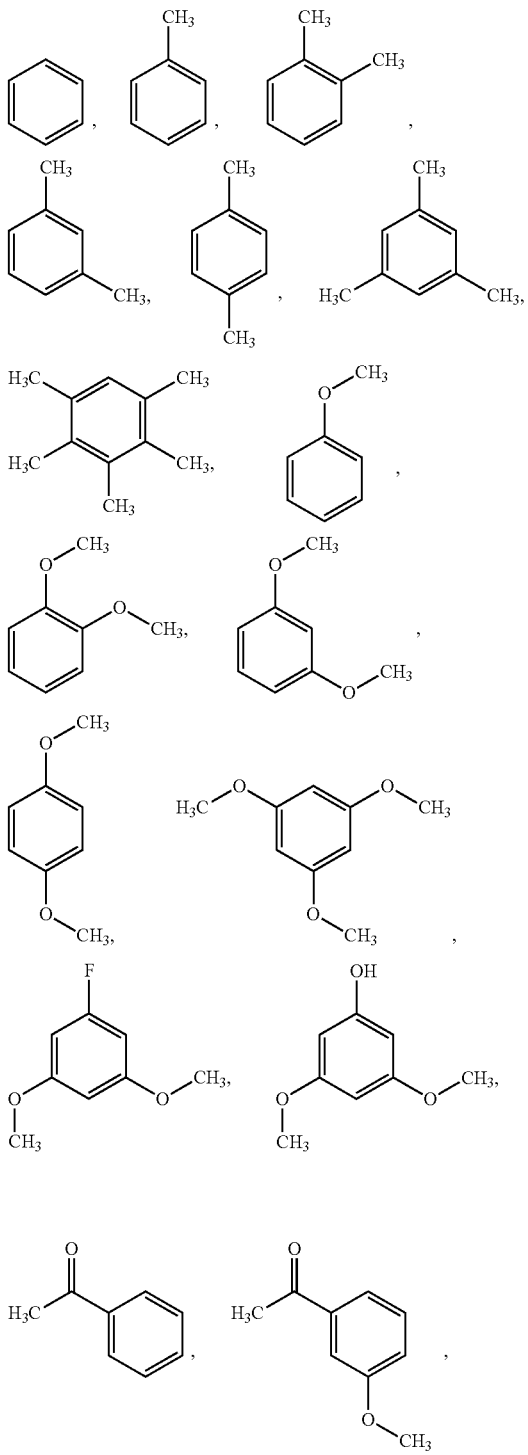

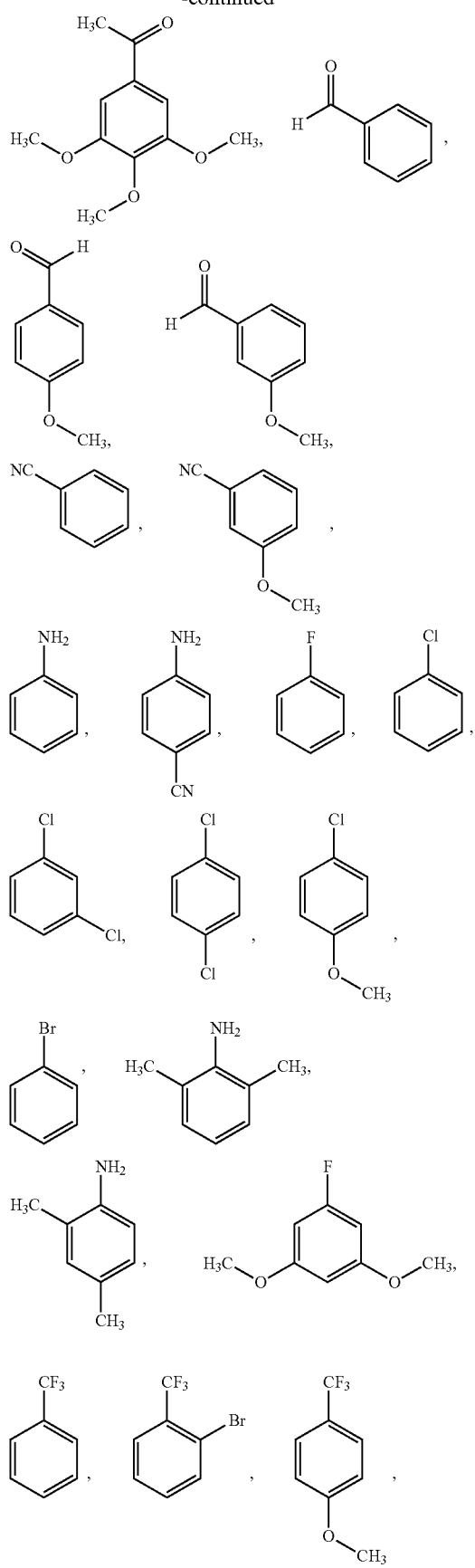
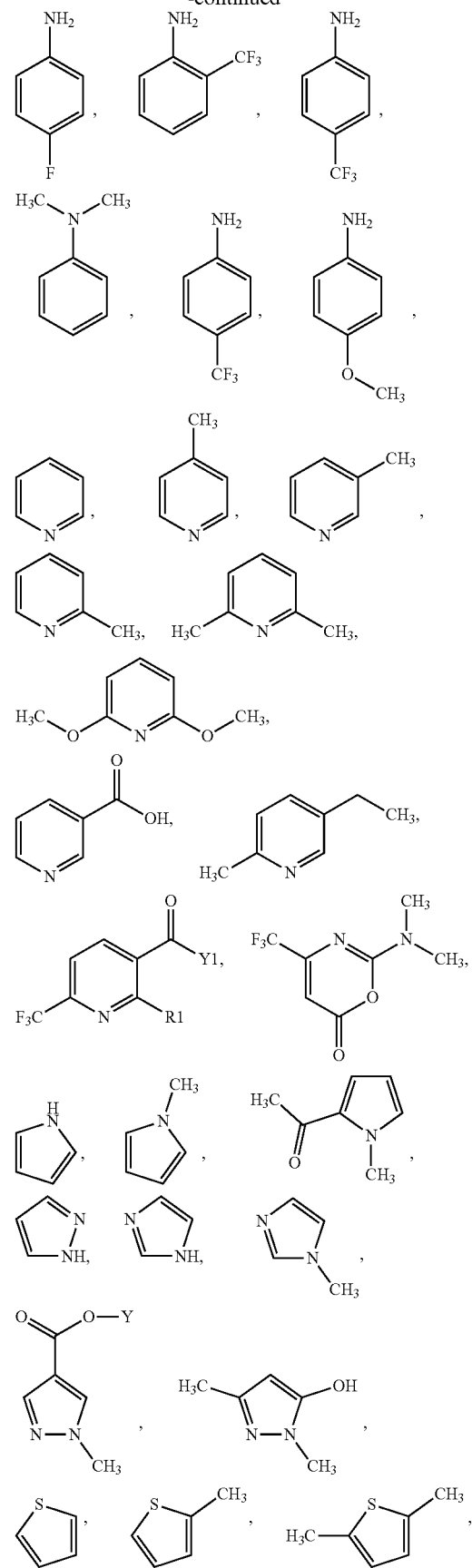

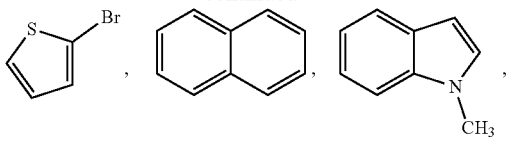

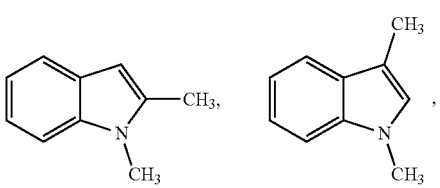

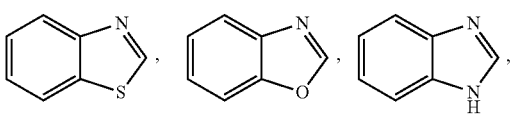

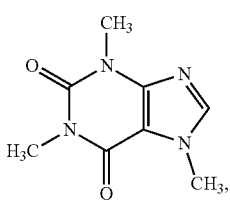

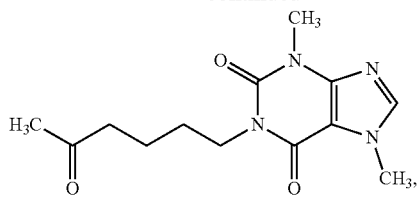

ethene, and polystyrene;
Y is $C_{1-6}$ alkyl;
the ethene being substituted by 1 substituent selected from the group consisting of $C_{1-10}$ alkyl.

7. The method according to claim 1, wherein
n3 is 2, 3, 4, 5, 6.

8. The method according to claim 1, wherein
FAHALIDE is selected from the group consisting of $F_{21}C_{10}$—I, $F_{21}C_{10}$—Br, $F_{17}C_8$—Br, $F_{13}C_6$—Br, $F_9C_4$—Br, $F_7C_3$—Br, $F_3C$—Br, Br—$(CF_2)_4$—Br, $F_2HC$—I, and $F_2HC$—Br.

9. The method according to claim 1, wherein
the reaction is done in the presence of a drying agent DRYAG;
wherein DRYAG is selected from the group consisting of molecular sieve and $Na_2SO_4$.

10. The method according to claim 1, wherein
the reaction is done neat or in a solvent SOL.

11. The method according to claim 10, wherein SOL is selected from the group consisting of alkanes, chlorinated alkanes, ketones, ethers, esters, aliphatic nitrils, aliphatic amides, sulfoxides, $C_6F_6$, and mixtures thereof.

* * * * *